United States Patent [19]
Etschenberg et al.

[11] 4,332,819
[45] Jun. 1, 1982

[54] ANTIPHLOGISTIC AGENT AND ITS USE

[75] Inventors: Eugen Etschenberg, Cologne; Haireddin Jacobi, Leichlingen; Wolfgang Opitz, Overath, all of Fed. Rep. of Germany

[73] Assignee: Troponwerke GmbH & Co. KG, Cologne, Fed. Rep. of Germany

[21] Appl. No.: 241,146

[22] Filed: Mar. 6, 1981

[30] Foreign Application Priority Data

Mar. 28, 1980 [DE] Fed. Rep. of Germany ....... 3011999

[51] Int. Cl.³ .......................................... A61K 31/265
[52] U.S. Cl. .................................................. 424/301
[58] Field of Search ......................................... 424/301

[56] References Cited

U.S. PATENT DOCUMENTS 4,246,278 1/1981 Opitz et al. ...................... 424/301

OTHER PUBLICATIONS

J. Chem. Soc. B, (1971), 565.

Primary Examiner—Stanley J. Friedman
Attorney, Agent, or Firm—Sprung, Horn, Kramer & Woods

[57] ABSTRACT

The invention relates to compositions containing S-benzyl 3-benzylthiopropionothioate for the treatment of inflammatory processes. Also included in the invention are methods for combating illnesses caused by inflammatory, processes, which methods involve use of medicaments containing said S-benzyl 3-benzylthiopropionothioate.

7 Claims, No Drawings

ANTIPHLOGISTIC AGENT AND ITS USE

The present invention relates to the use as medicaments for the treatment of inflammatory processes of S-benzyl 3-benzylthiopropionothioate of the formula

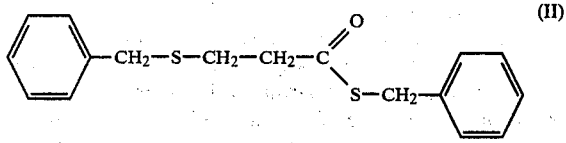

which is known.

The compound according to the invention has already been described as a chemical compound in the literature (see J. Chem. Soc. B 1971, 565).

It is also known that some sulphur-containing carboxylic acid derivatives have antiphlogistic actions (see DE-OS (German Published Specification) No. 2,753,768 and DE-OS (German Published Specification) No. 2,824,386).

Biological or pharmacological actions of the compound used according to the invention have not yet been disclosed.

According to the present invention there is provided a pharmaceutical composition containing as an active ingredient S-benzyl 3-benzylthiopropionothioate, in admixture with an inert pharmaceutical carrier, such as a solid or liquid gaseous diluent, or a liquid diluent other than a solvent of molecular weight less than 200 except in the presence of a surface active agent.

Surprisingly, the compound used according to the invention has a very powerful antiphlogistic action, coupled with good tolerance, both when applied intramuscularly and when applied orally. Furthermore, compared with the known sulphur-containing carboxylic acid derivatives, it has a less intensive odour and is thus considerably more suitable for pharmaceutical formulations and therapeutic use.

The antiphlogistic action was investigated on kaolin edemas in rat paws after oral and intramuscular administration (method: Vinegar, R., R. Pharmac. Exp. Ther., 161, 389, 1968). The compound according to the invention exhibits a significant antiphlogistic action even at dosages than 10 mg/kg or less, both when used parenterally and when used orally. It thus has a considerably more powerful action than commercially available antiphlogistic agents.

Investigation of the acute toxicity shows that the compound is very well tolerated by rats both after oral administration and after intramuscular administration ($LD_{50}$ greater than 1,000 mg/kg).

Since it is known that many antiphlogistic agents can lead to damage to the mucous membrane of the gastrointestinal tract, the ulcerogenic action of the compound in rats was also investigated. It is found that, in this case also, the compound used according to the invention is tolerated better than known antiphlogistic agents.

With knowledge of the state of the art, it could not be expected that S-benzyl 3-benzylthiopropionothioate, which is known, would have such a powerful action and be so well tolerated, and that this compound would be superior both to the chemically similar sulphur-containing carboxylic acid derivatives and to known active compounds which are employed as antiphlogistic agents.

The compound used according to the invention is prepared by known processes, preferably by reacting acrylyl chloride with benzylmercaptan and aqueous sodium hydroxide solution in a molar ratio of 1:2:1 in the presence of inert organic solvents, in particular dioxane, at temperatures between −10° and 40° C.

The two-phase reaction mixture is preferably worked up by extraction of the product by means of hydrophobic organic solvents, in particular methylene chloride, and subsequent distillation of the compound used according to the invention.

As stated above, the invention also relates to the use in medicine of the compound of the invention.

The present invention provides a pharmaceutical composition containing as active ingredient the compound of the invention together with an inert pharmaceutical carrier, such as a solid or liquefied gaseous diluent, or a liquid diluent other than a solvent of a molecular weight less than 200 (preferably less than 350) except in the presence of a surface active agent.

The invention also provides a medicament in dosage unit form comprising a compound of the invention and an inert pharmaceutical carrier.

The invention also provides a medicament in oral forms, e.g. in the form of tablets (including lozenges and granules), dragees, capsules, pills, amouples or suppositories comprising a compound of the invention. Also included are parenteral forms.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agaragar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and targacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or intramuscularly. Preferred pharmaceutical compositions and medicaments are therefore those adapted for administration such as oral or intramuscular administration. Administration in the method of the invention is preferably oral or intramuscular administration.

In general it has proved advantageous to administer orally amounts of from 100 to 4,000 mg/animal preferably 200 to 2,000 mg/animal per day, or to administer intramuscularly amount of from 10 to 1,500 mg/animal, preferably 50 to 800 mg/animal per day to achieve effective results. Where the active compound is administered in the form of several individual administrations, an individual administration preferably contains the active compound in amounts of from 10 to 300, preferably 50 to 200, mg/dose. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrates the preparation of the active compound S-benzyl 3-benzylthiopropionothioate used according to the present invention.

EXAMPLE 22 ml (0.27 mole) of acrylyl chloride were added dropwise to a mixture of 69 g (0.55 mole) of benzylmercaptan and 10.8 g (0.27 mole) of NaOH in 216 ml of water and 100 ml of dioxane, whilst cooling with ice and stirring. The two-phase reaction mixture was stirred overnight at room temperature and the product was extracted with methylene chloride and distilled in a bulb tube.

Yield: 53.05 g (64.9% of theory); boiling point $_{0.05}=240°-250°$ $^1$H-NMR (CDCl$_3$): δ ppm=2.65 (S, 2H); 3.62 (S, 2H); 4.03 (S, 2H); and 7.21 (S, 10H).

What is claimed is:

1. A pharmaceutical composition in solid form containing as an active ingredient an antiinflammatory effective amount of S-benzyl 3-benzylthiopropionothioate, in admixture with an inert pharmaceutical carrier.

2. A composition according to claim 1 containing from 0.5 to 95% of the said active ingredient, by weight.

3. A pharmaceutical composition for oral use in solution or suspension form containing as an active ingredient an antiinflammatory effective amount of S-benzyl 3-benzylthiopropionothioate, in admixture with an inert pharmaceutical carrier containing flavoring and sweetening agents.

4. A medicament of claim 3 in the form of tablets, pills, dragees, capsules, ampoules, or suppositories.

5. A method of combating illnesses caused by inflammatory processes in warm-blooded animals which comprises administering to the animals an antiinflammatory effective amount of S-benzyl 3-benzylthiopropionothioate either alone or in admixture with an inert pharmaceutical carrier or in the form of a medicament according to claim 3.

6. A method according to claim 5 in which the active compound is administered orally in an amount of from 200 to 2,000 mg/per animal per day.

7. A method according to claim 5 in which the active compound is adminstered intramuscularly in an amount of from 50 to 800 mg/per person per day.

* * * * *